United States Patent
Ito et al.

(10) Patent No.: US 10,220,150 B2
(45) Date of Patent: Mar. 5, 2019

(54) MANUFACTURING METHOD OF SYRINGE BARREL

(71) Applicant: MITSUBISHI GAS CHEMICAL COMPANY, INC., Tokyo (JP)

(72) Inventors: Hisafumi Ito, Kanagawa (JP); Takashi Kashiba, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 282 days.

(21) Appl. No.: 15/107,605

(22) PCT Filed: Feb. 9, 2015

(86) PCT No.: PCT/JP2015/053566
§ 371 (c)(1),
(2) Date: Jun. 23, 2016

(87) PCT Pub. No.: WO2015/119284
PCT Pub. Date: Aug. 13, 2015

(65) Prior Publication Data
US 2016/0325045 A1 Nov. 10, 2016

(30) Foreign Application Priority Data

Feb. 10, 2014 (JP) .................................. 2014-023104
Jun. 27, 2014 (JP) .................................. 2014-132140

(51) Int. Cl.
*A61M 5/31* (2006.01)
*B26D 3/00* (2006.01)
(Continued)

(52) U.S. Cl.
CPC ............ *A61M 5/31* (2013.01); *A61M 5/3129* (2013.01); *B26D 3/00* (2013.01); *B26D 7/08* (2013.01);
(Continued)

(58) Field of Classification Search
CPC .. A61M 5/31; A61M 5/3129; A61M 2205/02; A61M 2207/00; B26D 7/086;
(Continued)

(56) References Cited

U.S. PATENT DOCUMENTS 4,567,797 A  2/1986 Folk
4,685,602 A  8/1987 Hama
(Continued)

FOREIGN PATENT DOCUMENTS

CN  102858504  1/2013
JP  60-213499  10/1985
(Continued)

OTHER PUBLICATIONS

Machine Translation of JP-2012071441-A (Year: 2012).*
(Continued)

*Primary Examiner* — Matthew J Daniels
*Assistant Examiner* — Leith S Shafi
(74) *Attorney, Agent, or Firm* — Greenblum & Bernstein, P.L.C.

(57) ABSTRACT

The present invention provides a manufacturing method of a syringe barrel capable of securing smoothness of a nozzle tip and productivity. A manufacturing method of a syringe barrel that is injection-molded from a nozzle tip comprises cutting a remaining gate at a nozzle part using an ultrasonic cutting apparatus having a mechanism for suppressing abnormal vibrations.

6 Claims, 9 Drawing Sheets

(51) Int. Cl.
   *B26D 7/08*    (2006.01)
   *B29C 45/38*   (2006.01)
   *B29C 45/00*   (2006.01)
   B29C 45/16     (2006.01)
   B29L 31/00     (2006.01)
   B29K 23/00     (2006.01)

(52) U.S. Cl.
   CPC .......... *B26D 7/086* (2013.01); *B29C 45/0025* (2013.01); *B29C 45/38* (2013.01); *A61M 2205/02* (2013.01); *A61M 2207/00* (2013.01); *B29C 45/16* (2013.01); *B29C 2045/0027* (2013.01); *B29C 2793/009* (2013.01); *B29K 2023/38* (2013.01); *B29L 2031/7544* (2013.01)

(58) Field of Classification Search
   CPC ... B26D 7/08; B26D 3/00; B26D 3/16; B26D 3/166; B29C 45/0025; B29C 45/38; B29C 45/16; B29C 2793/009; B29C 2045/0027; B29K 2023/38; B29L 2031/7544
   USPC .................. 83/766, 767, 469, 491–495, 663, 83/674–675, 284–297; 264/442
   See application file for complete search history.

(56) References Cited

U.S. PATENT DOCUMENTS

| | | | | |
|---|---|---|---|---|
| 7,012,767 B2* | 3/2006 | Yamamoto | .............. | B29C 45/27 359/718 |
| 7,093,525 B2* | 8/2006 | Proffitt | .................... | B29C 49/74 82/46 |
| 2001/0007513 A1* | 7/2001 | Koshimizu | ......... | B29C 45/0055 359/811 |
| 2002/0174758 A1* | 11/2002 | Harikawa | .............. | B23D 45/26 83/835 |
| 2004/0267194 A1 | 12/2004 | Sano et al. | | |
| 2008/0271870 A1 | 11/2008 | Yotsutsuji | | |
| 2012/0182624 A1* | 7/2012 | Itou | .................. | B29D 11/00432 359/642 |
| 2013/0152757 A1* | 6/2013 | Nakai | .................. | B26D 1/0006 83/601 |
| 2014/0054829 A1* | 2/2014 | Poo | ......................... | B29B 11/14 264/533 |

FOREIGN PATENT DOCUMENTS

| | | |
|---|---|---|
| JP | 63-16916 | 1/1988 |
| JP | 5-300939 | 11/1993 |
| JP | 5-317411 | 12/1993 |
| JP | 10-296687 | 11/1998 |
| JP | 11216752 A * | 8/1999 |
| JP | 2004-229750 | 8/2004 |
| JP | 2009-291901 | 12/2009 |
| JP | 2012071441 A * | 4/2012 |
| JP | 2012-106329 | 6/2012 |
| WO | 2005/011954 | 2/2005 |

OTHER PUBLICATIONS

Translation of JP-11216752-A (Year: 1999).*
International Preliminary Report on Patentability issued in PCT/JP2015/053566, dated Aug. 16, 2016.
International Search Report issued in Japanese Patent Application No. PCT/JP2015/053566, dated Apr. 28, 2015.

* cited by examiner

FIG. 6A

TABLE 2-1

| | THERMO-PLASTIC RESIN (b) | ABNORMAL VIBRATION SUPPRESSING MECHANISM | CUTTING STEPS FIRST CUTTING | | |
|---|---|---|---|---|---|
| | | | CUTTING STEPS | STOP OF CUTTING A) | ANGLE (S) [°] |
| EXAMPLE 1 | COP | PRESENT | PRESENT | 50 | 90 |
| EXAMPLE 2 | COP | PRESENT | NOT PRESENT | | |
| EXAMPLE 3 | COP | PRESENT | PRESENT | 50 | 90 |
| EXAMPLE 4 | COP | PRESENT | PRESENT | 50 | 90 |
| EXAMPLE 5 | COP | PRESENT | NOT PRESENT | | |
| EXAMPLE 6 | COP | PRESENT | PRESENT | 50 | 90 |
| EXAMPLE 7 | COP | PRESENT | PRESENT | 50 | 90 |
| EXAMPLE 8 | COP | PRESENT | PRESENT | 50 | 90 |
| EXAMPLE 9 | COP | PRESENT | PRESENT | 50 | 90 |
| EXAMPLE 10 | PP | PRESENT | PRESENT | 50 | 90 |
| EXAMPLE 11 | PP | PRESENT | NOT PRESENT | | |
| EXAMPLE 12 | PP | PRESENT | PRESENT | 80 | 50 |
| EXAMPLE 13 | PP | PRESENT | PRESENT | 50 | 90 |
| EXAMPLE 14 | PP | PRESENT | NOT PRESENT | | |
| EXAMPLE 15 | COP (MONOLAYER) | PRESENT | PRESENT | 50 | 90 |
| EXAMPLE 16 | COP (MONOLAYER) | PRESENT | PRESENT | 50 | 90 |
| EXAMPLE 17 | COP | PRESENT | NOT PRESENT | | |
| EXAMPLE 18 | COP | PRESENT | NOT PRESENT | | |
| EXAMPLE 19 | COP | PRESENT | NOT PRESENT | | |
| COMPARATIVE EXAMPLE 1 | COP | NOT PRESENT | NOT PRESENT | | |
| COMPARATIVE EXAMPLE 2 | COP | NOT PRESENT | PRESENT | 10 | 110 |
| COMPARATIVE EXAMPLE 3 | COP | NOT PRESENT | NOT PRESENT | | |

A) RATIO OF A CUT PORTION TO THE OUTER DIAMETER OF AN OBJECT TO BE CUT.
B) CUTTING DISTANCE FROM A PREVIOUSLY-CUT SURFACE

FIG. 6B

TABLE.2-2

| | THERMO-PLASTIC RESIN (b) | ABNORMAL VIBRATION SUPPRESS-ING MECHA-NISM | CUTTING DISTANCE B)[mm] | CUTTING STEPS SECOND CUTTING | | |
|---|---|---|---|---|---|---|
| | | | | CUTTING STEPS | STOP OF CUTTING A) | ANGLE (S) [°] |
| EXAMPLE1 | COP | PRESENT | 0.5 | NOT PRESENT | | |
| EXAMPLE2 | COP | PRESENT | 0.6 | NOT PRESENT | | |
| EXAMPLE3 | COP | PRESENT | 0.3 | NOT PRESENT | | |
| EXAMPLE4 | COP | PRESENT | 0.5 | PRESENT | 50 | 90 |
| EXAMPLE5 | COP | PRESENT | 0.6 | NOT PRESENT | | |
| EXAMPLE6 | COP | PRESENT | 0.5 | PRESENT | 50 | 90 |
| EXAMPLE7 | COP | PRESENT | 0.5 | PRESENT | 50 | 90 |
| EXAMPLE8 | COP | PRESENT | 0.5 | PRESENT | 50 | 90 |
| EXAMPLE9 | COP | PRESENT | 0.5 | PRESENT | 50 | 90 |
| EXAMPLE10 | COP | PRESENT | 0.2 | PRESENT | 50 | 90 |
| EXAMPLE11 | COP | PRESENT | 0.8 | PRESENT | 25 | 7 |
| EXAMPLE12 | COP | PRESENT | | | | |
| EXAMPLE13 | PP | PRESENT | 0.5 | NOT PRESENT | | |
| EXAMPLE14 | PP | PRESENT | 0.5 | NOT PRESENT | | |
| EXAMPLE15 | PP | PRESENT | 0.4 | NOT PRESENT | | |
| EXAMPLE16 | PP | PRESENT | 0.8 | PRESENT | 25 | 7 |
| EXAMPLE17 | PP | PRESENT | | | | |
| EXAMPLE18 | COP (MONOLAYER) | PRESENT | 0.6 | NOT PRESENT | | |
| EXAMPLE19 | COP | PRESENT | 0.8 | PRESENT | 75 | 45 |
| COMPARATIVE EXAMPLE1 | COP | NOT PRESENT | | | | |
| COMPARATIVE EXAMPLE2 | | NOT PRESENT | | | | |
| COMPARATIVE EXAMPLE3 | | NOT PRESENT | 4 | NOT PRESENT | | |

A) RATIO OF A CUT PORTION TO THE OUTER DIAMETER OF AN OBJECT TO BE CUT.
B) CUTTING DISTANCE FROM A PREVIOUSLY-CUT SURFACE

FIG. 6C

TABLE 2-3

| | THERMO-PLASTIC RESIN (b) | ABNORMAL VIBRATION SUPPRESS-ING MECHA-NISM | CUTTING STEPS | | |
|---|---|---|---|---|---|
| | | | CUTTING DISTANCE B) [mm] | THIRD CUTTING | |
| | | | | CUTTING STEPS | STOP OF CUTTING A) |
| | | | | | ANGLE (S) [°] |
| EXAMPLE1 | COP | PRESENT | 0.2 | NOT PRESENT | | |
| EXAMPLE2 | | PRESENT | 0.2 | NOT PRESENT | | |
| EXAMPLE3 | | PRESENT | 0.1 | NOT PRESENT | | |
| EXAMPLE4 | | PRESENT | 0.1 | PRESENT | 50 | 90 |
| EXAMPLE5 | | PRESENT | 0.1 | PRESENT | 8 | 20 |
| EXAMPLE6 | | PRESENT | 0.1 | PRESENT | 8 | 20 |
| EXAMPLE7 | | PRESENT | 0.2 | PRESENT | 25 | 25 |
| EXAMPLE8 | | PRESENT | 0.2 | PRESENT | 45 | 25 |
| EXAMPLE9 | | PRESENT | 0.2 | PRESENT | 45 | 8 |
| EXAMPLE10 | | PRESENT | 0.45 | PRESENT | 25 | 25 |
| EXAMPLE11 | | PRESENT | | | | |
| EXAMPLE12 | PP | PRESENT | | | | |
| EXAMPLE13 | | PRESENT | 0.2 | NOT PRESENT | | |
| EXAMPLE14 | | PRESENT | 0.1 | NOT PRESENT | | |
| EXAMPLE15 | | PRESENT | 0.2 | PRESENT | 73 | 115 |
| EXAMPLE16 | | PRESENT | | | | |
| EXAMPLE17 | | PRESENT | | | | |
| EXAMPLE18 | COP (MONOLAYER) | PRESENT | 0.2 | NOT PRESENT | | |
| EXAMPLE19 | | PRESENT | | | | |
| COMPARATIVE EXAMPLE1 | | NOT PRESENT | | | | |
| COMPARATIVE EXAMPLE2 | COP | NOT PRESENT | | | | |
| COMPARATIVE EXAMPLE3 | | NOT PRESENT | | | | |

A) RATIO OF A CUT PORTION TO THE OUTER DIAMETER OF AN OBJECT TO BE CUT.
B) CUTTING DISTANCE FROM A PREVIOUSLY-CUT SURFACE

FIG. 6D

TABLE 2-4

| | THERMO-PLASTIC RESIN (b) | ABNORMAL VIBRATION SUPPRESSING MECHANISM | CUTTING STEPS | | | | FINAL CUTTING LOAD [N] |
|---|---|---|---|---|---|---|---|
| | | | FOURTH CUTTING | | | | |
| | | | CUTTING DISTANCE B) [mm] | CUTTING STEPS | STOP OF CUTTING A) | ANGLE (S) [°] | |
| EXAMPLE1 | COP | PRESENT | 0.1 | NOT PRESENT | | | 40 |
| EXAMPLE2 | | PRESENT | 0.1 | NOT PRESENT | | | 55 |
| EXAMPLE3 | | PRESENT | 0.05 | PRESENT | 85 | 45 | 30 |
| EXAMPLE4 | | PRESENT | 0.05 | PRESENT | 75 | 60 | 70 |
| EXAMPLE5 | | PRESENT | | | | | 55 |
| EXAMPLE6 | | PRESENT | | | | | 45 |
| EXAMPLE7 | | PRESENT | | | | | 115 |
| EXAMPLE8 | | PRESENT | | | | | 123 |
| EXAMPLE9 | | PRESENT | | | | | 125 |
| EXAMPLE10 | | PRESENT | | | | | 160 |
| EXAMPLE11 | | PRESENT | | | | | 230 |
| EXAMPLE12 | | PRESENT | | | | | 320 |
| EXAMPLE13 | PP | PRESENT | 0.1 | NOT PRESENT | | | 30 |
| EXAMPLE14 | | PRESENT | | | | | 35 |
| EXAMPLE15 | | PRESENT | | | | | 70 |
| EXAMPLE16 | | PRESENT | | | | | 240 |
| EXAMPLE17 | | PRESENT | | | | | 370 |
| EXAMPLE18 | COP (MONOLAYER) | PRESENT | 0.1 | NOT PRESENT | | | 60 |
| EXAMPLE19 | COP | PRESENT | | | | | 220 |
| COMPARATIVE EXAMPLE1 | | NOT PRESENT | | | | | 600 |
| COMPARATIVE EXAMPLE2 | | NOT PRESENT | | | | | 550 |
| COMPARATIVE EXAMPLE3 | | NOT PRESENT | | | | | 540 |

A) RATIO OF A CUT PORTION TO THE OUTER DIAMETER OF AN OBJECT TO BE CUT.
B) CUTTING DISTANCE FROM A PREVIOUSLY-CUT SURFACE

FIG. 7

TABLE 3

| | CUTTING PATTERN | SURFACE ROUGHNESS Ra [μm] | CUTTING TIME [SEC] | EVALUATION | | | |
|---|---|---|---|---|---|---|---|
| | | | | APPEARANCE c) | BURR/ MELTING | CRACK IN NOZZLE PART | TOTAL EVALUATION SCORE |
| EXAMPLE1 | <E> | 0.25 | 16 | EXCELLENT | NOT PRESENT | NOT PRESENT | A |
| EXAMPLE2 | <C> | 0.45 | 13 | GOOD | NOT PRESENT | NOT PRESENT | B |
| EXAMPLE3 | <F> | 0.11 | 18 | EXCELLENT | NOT PRESENT | NOT PRESENT | A |
| EXAMPLE4 | <F> | 0.29 | 32 | EXCELLENT | NOT PRESENT | NOT PRESENT | B |
| EXAMPLE5 | <D> | 1.05 | 15 | GOOD | NOT PRESENT | NOT PRESENT | B |
| EXAMPLE6 | <F> | 0.60 | 25 | GOOD | NOT PRESENT | NOT PRESENT | B |
| EXAMPLE7 | <F> | 1.30 | 25 | GOOD | NOT PRESENT | NOT PRESENT | B |
| EXAMPLE8 | <F> | 1.70 | 25 | ACCEPTABLE | NOT PRESENT | NOT PRESENT | C |
| EXAMPLE9 | <F> | 2.10 | 25 | ACCEPTABLE | NOT PRESENT | NOT PRESENT | C |
| EXAMPLE10 | <F> | 2.31 | 25 | ACCEPTABLE | NOT PRESENT | NOT PRESENT | C |
| EXAMPLE11 | <C> | 2.25 | 14 | ACCEPTABLE | NOT PRESENT | NOT PRESENT | C |
| EXAMPLE12 | <B> | 2.79 | 9 | ACCEPTABLE | NOT PRESENT | NOT PRESENT | C |
| EXAMPLE13 | <E> | 0.37 | 16 | EXCELLENT | NOT PRESENT | NOT PRESENT | A |
| EXAMPLE14 | <C> | 1.10 | 11 | GOOD | NOT PRESENT | NOT PRESENT | B |
| EXAMPLE15 | <F> | 0.50 | 23 | GOOD | NOT PRESENT | NOT PRESENT | B |
| EXAMPLE16 | <F> | 2.50 | 12 | ACCEPTABLE | NOT PRESENT | NOT PRESENT | C |
| EXAMPLE17 | <A> | 2.80 | 6 | ACCEPTABLE | NOT PRESENT | NOT PRESENT | C |
| EXAMPLE18 | <C> | 0.48 | 13 | GOOD | NOT PRESENT | NOT PRESENT | B |
| EXAMPLE19 | <F> | 2.35 | 14 | ACCEPTABLE | NOT PRESENT | NOT PRESENT | C |
| COMPARATIVE EXAMPLE1 | | 6.21 | | UNACCEPTABLE | PRESENT | PRESENT | UNACCEPTABLE |
| COMPARATIVE EXAMPLE2 | | 3.20 | | UNACCEPTABLE | PRESENT | NOT PRESENT | UNACCEPTABLE |
| COMPARATIVE EXAMPLE3 | | 4.50 | | UNACCEPTABLE | PRESENT | NOT PRESENT | UNACCEPTABLE | c) EXCELLENT: NO MOLTEN TRACE OR MARK OBSERVED.
GOOD: SLIGHT MOLTEN TRACES OR MARKS WERE OBSERVED.
ACCEPTABLE: MOLTEN TRACES OR MARKS WERE OBSERVED BUT THE SURFACE ROUGHNESS SATISFIED A SPECIFIED LEVEL.
UNACCEPTABLE: MOLTEN TRACES OR MARKS WERE OBSERVED AND THE SURFACE ROUGHNESS DID NOT SATISFY A SPECIFIED LEVEL.

FIG. 8A

TABLE 4-1

| EVALUATION ITEMS | CRITERIA | SCORE |
|---|---|---|
| SURFACE ROUGHNESS | 0.3 μm OR LESS | 3 |
| | GREATER THAN 0.3 AND 1.0 OR LESS | 2 |
| | GREATER THAN 1.0 AND 2.0 OR LESS | 1 |
| | GREATER THAN 2.0 AND 3.0 OR LESS | 0 |
| CUTTING TIME | 18 SECONDS OR SHORTER | 3 |
| | LONGER THAN 18 SECONDS AND 30 SECONDS OR SHORTER | 2 |
| | LONGER THAN 30 SECONDS | 1 |
| APPEARANCE | EXCELLENT | 3 |
| | GOOD | 2 |
| | ACCEPTABLE | 1 |

AFTER GIVING SCORES FOR THE EVALUATION ITEMS,
TOTAL EVALUATION IS MADE BASED ON THE TABLE BELOW

FIG. 8B

TABLE 4-2

| TOTAL EVALUATION | SCORE |
|---|---|
| A | 8 OR HIGHER |
| B | 5 TO 7 |
| C | 4 OR LOWER |

MANUFACTURING METHOD OF SYRINGE BARREL

TECHNICAL FIELD

The present invention relates to a manufacturing method of a syringe barrel, more specifically to a manufacturing method of a syringe barrel with a nozzle tip having excellent smoothness.

BACKGROUND ART

A conventional glass syringe is being replaced with a resin syringe and, in a disposable syringe, a resin syringe is becoming more popular for hygienic and disposal reasons. In addition, prefilled syringe formulations are becoming prevalent in the medical field for the reason that, for example, prefilled syringe formulations eliminate the effort required in a conventional injection of pouring a drug from another container, such as a vial or an ampoule, into a syringe, and enable easier aseptic preparation. However, since a conventional resin container tends to be more oxygen permeable, unlike a glass bottle and a metallic container, the resin container still has a problem in terms of the storage stability of its content after filling and sealing the resin container and the replacement thereof with such resin containers has not actually made strong progress. Therefore, recently, there has been a need for replacement of glass syringes, which have been used for a long time, with resin syringes.

In general, when a syringe barrel is molded, a method of forming two gates in a flange or two gates in a body part is commonly used in order to secure the circularity of a cylindrical part. However, such molding method has a disadvantage in that welded parts are formed and the mechanical strength of the syringe barrel is lowered. On the other hand, if injection is performed from a nozzle part, mechanical strength can be secured without the formation of any welded part and circularity can also be secured. Further, if there is only one gate, the runner balance in a mold can be adjusted easily and the number of cavities per volume can be increased. However, if a syringe barrel is molded by performing injection from a nozzle part, a remaining gate at the nozzle part has to be cut by a certain method. As a known technique in a method of cutting a resin tube, a rotary blade or grinding wheel may be used. However, such method produces chips. Since a syringe barrel is produced in a clean room, the generation of chips in cutting the remaining gate at the nozzle part will require a dedicated booth or dust collector or require a cleaning apparatus for removing the chips inside the nozzle, which is not economical.

In order to solve this problem, a proposed manufacturing method includes the use of equipment having a structure in which, for example, in an extrusion manufacturing line of a synthetic resin tube, a force-cutting blade is rotated around the synthetic resin tube to cut the synthetic resin tube, while a press roll, which is provided separately from the force-cutting blade, is rotated around the synthetic resin tube so as to follow the force-cutting blade with the press roll being positioned on a cutting line of the tube, in order to suppress the generation of chips (see Patent document 1).

On the other hand, in a plastic bottle for foods and beverages in a technical field in which the replacement of glass with resin has made progress, the storage stability of content after filling and sealing the plastic bottle has been improved by co-extruding a preform including polyethylene terephthalate resin in a skin layer and a thermoplastic resin having a gas barrier property in a core layer and then performing blow molding. A molding method using such technique has been proposed, in which a polyolefin resin and a barrier resin are subjected to coinjection molding with a gate being located on a nozzle side of a barrel to produce a barrel having a multilayer structure having an innermost layer and an outermost layer formed of the polyolefin resin and a core layer formed of the barrier resin, and the molding is performed with an open nozzle of an injection unit being in close contact with a nozzle tip surface in order to avoid any remaining gate (Patent Document 2).

CITATION LIST

Patent Document

Patent Document 1: JPH10-296687 A
Patent Document 2: JP2004-229750 A

SUMMARY

Technical Problem

The method described in Patent Document 1 is a method suited for products having a constant outer diameter, such as extrusion-molded products, and there is a difficulty in applying such method to a syringe barrel as the syringe barrel has a step between a nozzle part and a body part and the nozzle part is tapered so as to be formed in a conical shape. Furthermore, the syringe barrel is continuously rotated if such method is applied, and the surface of the syringe barrel will be damaged.

Patent Document 2 proposes a molding method in which the open nozzle of the injection unit is brought into close contact with the nozzle tip surface in order to avoid any remaining gate. However, since the number of cavities in the mold is limited to one per injection unit in such method, the productivity is poor. In addition, stringing of resin is likely to occur when the molded product is removed from the mold, which makes it impossible to maintain the smoothness of the nozzle tip surface and causes yield to be lowered. Furthermore, although a molding method of allowing the nozzle gate to be left has also been proposed, no description has been provided regarding a cutting method.

The present invention has been made in light of the above circumstances and an object of the present invention is to provide a manufacturing method of a syringe barrel capable of preventing the generation of chips and securing smoothness of a nozzle tip and productivity in equal levels to those of the case in which cutting is performed by a known method using a rotary blade, a grinding wheel, etc.

Solution to Problem

After the intensive study, the inventors have found that, by using an ultrasonic cutting apparatus having a mechanism for suppressing abnormal vibrations to perform cutting, it is possible to obtain a cut surface having a surface roughness equal to that obtained when a known technique using a rotary blade, a grinding wheel, etc. is used to perform cutting, without generating chips.

The present invention provides the following <1> to <8>.

<1> A manufacturing method of a syringe barrel that is injection-molded from a nozzle tip, the method comprising cutting a remaining gate at a nozzle part using an ultrasonic cutting apparatus having a mechanism for suppressing abnormal vibrations.

<2> The manufacturing method according to <1>, comprising, during the cutting of the remaining gate at the nozzle part, performing cutting a plurality of times.

<3> The manufacturing method according to <2> comprising, during the cutting of the remaining gate at the nozzle part, temporarily stopping cutting after cutting part of a circumference of the nozzle part of the syringe barrel, relatively rotating an ultrasonic cutting blade of the ultrasonic cutting apparatus and the syringe barrel, and cutting another portion in the circumference of the nozzle part.

<4> The manufacturing method according to <3>, comprising: in a final cutting step (2), (2-1) temporarily stopping cutting after cutting part of the circumference of the nozzle part of the syringe barrel using the ultrasonic cutting apparatus; and (2-2) relatively rotating the ultrasonic cutting blade and the syringe barrel to a positional relationship in which an arc of an outer diameter of an uncut portion does not exist at an intersection (P) that is more distant from the ultrasonic cutting blade surface from among two intersections between an outer diameter circle of a cross-section of the nozzle part and a line segment that is perpendicular to a cutting edge of the ultrasonic cutting blade and that passes a center of the outer diameter circle of the cross-section of the nozzle part, and then performing cutting of the uncut portion.

<5> according to comprising, <3>, comprising, when the final cutting step (2) is performed after the remaining gate at the nozzle part is cut with a finishing allowance being left in an initial cutting step (1), during the cutting of the remaining gate at the nozzle part in the initial cutting step, temporarily stopping the cutting after cutting part of the remaining gate at the nozzle part, relatively rotating the ultrasonic cutting blade and the syringe barrel, and cutting another portion in the remaining gate at the nozzle part.

<6> The manufacturing method according to any one of <1> to <5>, wherein the syringe barrel has a multilayer structure having at least three resin layers.

<7> The manufacturing method according to any one of <1> to <6>, wherein, during the final cutting of the syringe barrel, a load applied to the ultrasonic cutting blade is from 1 to 400 N.

<8> The manufacturing method according to any one of <1> to <7>, wherein, in the final cutting step (2), a distance from a previously cut surface to a cutting position is from 0.1 to 1 mm.

Advantageous Effects of Invention

According to the present invention, it is possible to manufacture a syringe barrel with a cut surface having excellent smoothness without generating chips.

BRIEF DESCRIPTION OF DRAWINGS

FIG. 6A is a divided table showing cutting conditions (cutting steps) of the remaining gate at the nozzle part in the Examples and Comparative Examples of the present invention.

FIG. 6B is a divided table showing cutting conditions (cutting steps) of the remaining gate at the nozzle part in the Examples and Comparative Examples of the present invention.

FIG. 6C is a divided table showing cutting conditions (cutting steps) of the remaining gate at the nozzle part in the Examples and Comparative Examples of the present invention.

FIG. 6D is a divided table showing cutting conditions (cutting steps) of the remaining gate at the nozzle part in the Examples and Comparative Examples of the present invention.

FIG. 7 is a table showing cutting patterns and evaluations of a remaining gate at a nozzle part in the Examples and Comparative Examples of the present invention.

FIG. 8A shows a table (Table 4-1) which shows evaluation items, criteria and scores.

FIG. 8B shows a table (Table 4-2) which shows the content of a total evaluation, regarding the cutting of a remaining gate at a nozzle part in the Examples and Comparative Examples of the present invention.

DESCRIPTION OF EMBODIMENTS

Embodiments of the present invention will now be described with reference to the attached drawings. It should be noted that, although a syringe barrel having a shape compliant with ISO standards will be described in the following embodiments, such shape is only an example for explaining the present invention. The present invention is not limited to the embodiments and is also applicable to shapes other than those compliant with the ISO standards and to multilayer structures.

Shape of Syringe Barrel

Figure 1:
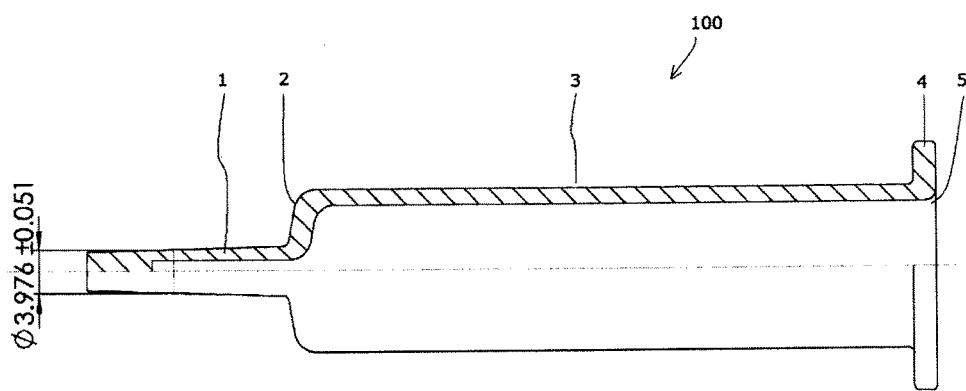
FIG. 1 is a half-sectional view showing a monolayer syringe barrel before cutting a remaining gate at a nozzle part, according to an embodiment of the present invention.

A monolayer syringe barrel 100 shown in FIG. 1 has a standard shape having an internal capacity of 5 cc which is compliant with ISO 11040-6. Specifically, the syringe barrel 100 comprises, from its tip side, a nozzle part 1 that allows an injection needle to be connected thereto, a shoulder part 2 and a cylindrical part 3. The cylindrical part 3 is constituted by a portion having a constant diameter in a direction along the central axis X-X of the syringe barrel 100 and the cylindrical part 3 has a flange 5 at an opening end (a cylindrical part base end 4). The nozzle part 1 is constituted by a portion having a smaller diameter than the cylindrical part 3 and formed so as to be tapered in compliance with ISO 594-1. The shoulder part 2 is a portion connecting between the nozzle part 1 and the cylindrical part 3 on a side opposite to the cylindrical part base end 4. The syringe barrel 100 is formed so that the nozzle part 1, the shoulder part 2 and the cylindrical part 3 are formed in an integral manner by injection molding from the tip side of the nozzle 1 with a gate remaining at the nozzle part.

Figure 2:
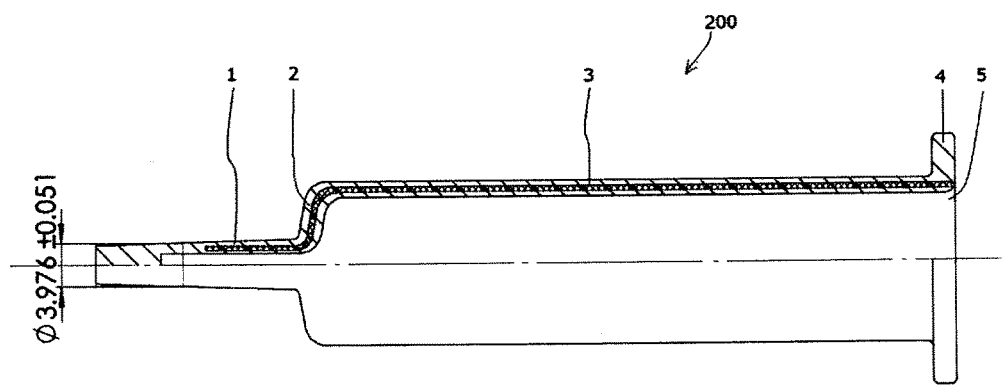
FIG. 2 is a half-sectional view showing a multilayer syringe barrel before cutting a remaining gate at a nozzle part, according to an embodiment of the present invention.
Figure 3:
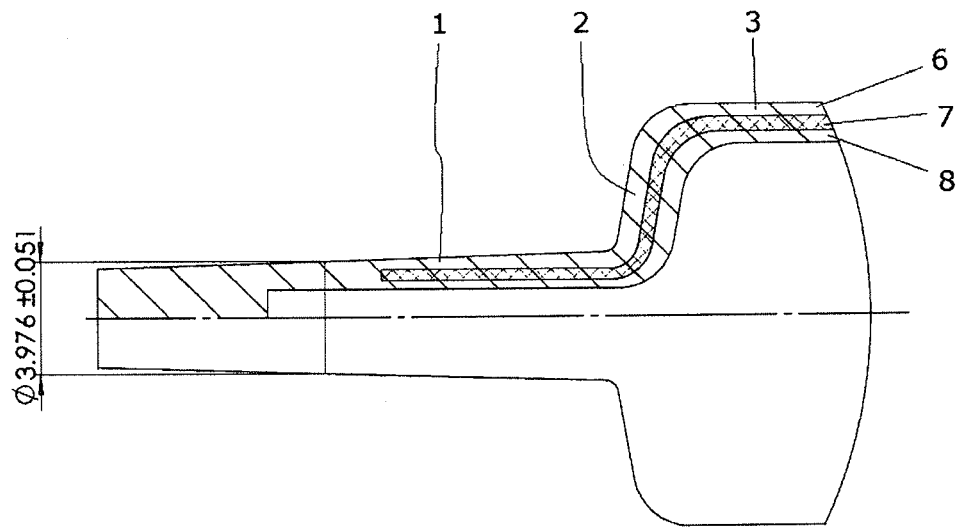
FIG. 3 is an enlarged view showing the vicinity of the nozzle part in the multilayer syringe barrel before cutting the remaining gate at the nozzle part, according to an embodiment of the present invention.

As shown in FIG. 2, a multilayer syringe barrel 200 has the same shape as the syringe barrel 100. The multilayer syringe barrel 200 is formed by injection molding from the tip side of the nozzle part 1 and has a structure comprising a first resin layer (skin layer) 6 formed of a first thermoplastic resin composition (b), a second resin layer (core layer) 7 formed of a barrier thermoplastic resin composition (a), and a third resin layer (skin layer) 8 formed of the first thermoplastic resin composition (b), in the order mentioned. The first resin layer 6 and the third resin layer 8 constitute the outermost layer and the innermost layer, respectively, of the multilayer syringe barrel 200 and the second resin layer 7 constitutes an intermediate layer of the multilayer syringe barrel 200. If the injection molding is performed by locating the gate at a position other than the nozzle, such as in the cylindrical part 3 or in the flange part 5, the cylindrical part cannot be formed uniformly due to, for example, the formation of a weld or a gap in the second resin layer (core layer) 7. In the nozzle part, a cutting position is determined so as to fall within a range of $\phi 3.976+/-0.051$, as specified in ISO 594-1. Although the second resin layer extends from a position on the flange side with respect to a gasket inserting position in the cylindrical part, to a position of the nozzle part, an end edge of the second resin layer is preferably located at a position that is not exposed to the outside at the cutting position, in order to prevent the second resin layer from being eluted due to contact with a drug solution when the drug solution is discharged.

Cutting of Remaining Gate at Nozzle Part

The ultrasonic cutting apparatus used in the present invention is not particularly limited and any known cutting apparatus may be used as long as it has a mechanism for suppressing abnormal vibrations. The abnormal vibrations as used herein refer to a vibration component, such as transverse wobbling, in a direction different from a vibration direction parallel to a cutting blade. If an ultrasonic cutting apparatus without the mechanism for suppressing abnormal vibrations is used to perform cutting, heat is likely to be generated between a blade surface and resin on an already-cut surface during cutting and the smoothness of the cut surface cannot be secured.

It is considered that a problem occurs when the vibration component in a direction different from the natural vibration direction of an oscillator parallel to the cutting blade is applied to the cutting blade. Specifically, minute transverse wobbling that is irrelevant to the vibration of the oscillator is generated in a resonator body due to a supporting structure of the resonator, a vibration component, such as the transverse wobbling, in a direction different from the natural vibration direction of the oscillator, in other words, a vibration component such as the transverse wobbling in a direction different from the vibration direction parallel to the cutting blade is generated in the resonator, and when the vibration component, such as the transverse wobbling in the direction different from the natural vibration direction (in the present specification, vibration which is irrelevant to the vibration of the oscillator, such as transverse wobbling, is referred to as "abnormal vibration"), which is generated in the resonator is applied to the cutting blade, some problems occur—for example, a cutting edge is bent when an object is cut, chipping or breakage occurs in a cut piece from the object due to the transverse wobbling of the cutting edge of the cutting blade which results from the abnormal vibrations, and so on. In addition, an entering angle of the cutting edge into the object is not stable due to the transverse wobbling of the cutting blade and when a minute displacement is generated in the position of contact between the cutting edge of the cutting blade and the object occurs due to the transverse wobbling of the cutting edge, the cutting edge may obliquely enter the object, which may cause the cutting blade to be bent. In such case, although the displacement of the contact position between the cutting edge and the object is minute, a large positional displacement is generated in a cut surface of the object cut by the cutting blade and the appearance of the cut surface is disadvantageously deteriorated.

The ultrasonic cutting apparatus preferably comprises a mechanism capable of positioning a seat on which an object to be cut is placed when an ultrasonic cutting blade moves up and down. In addition, a jig for fixing the syringe barrel preferably has a structure for supporting the vicinity of a cutting position in the nozzle part. The ultrasonic apparatus having the mechanism for suppressing the abnormal vibrations is described in, for example, JP2012-106329 A and an example of a specific product is ultrasonic cutter UC1000LS manufactured by ADWELDS CORPORATION.

As an example, the apparatus having the mechanism for suppressing abnormal vibrations described in JP2012-106329 A is a vibration cutting apparatus for cutting an object by applying vibrations to a cutting blade, the vibration cutting apparatus comprising: a resonator having one end connected to an oscillator and the other end, on the opposite side of the oscillator, having an attachment part to which the cutting blade is attached; and support means that comprises a grasping part for grasping a portion to be grasped in the resonator to support the resonator, in which at least one elongated hole is provided through a lateral surface of the resonator. In this vibration cutting apparatus, the support means supports the resonator by grasping the portion to be grasped with the grasping part and by supporting the resonator rigidly, using the grasping part of the support means without using an elastic vibration absorbing material used in a conventional apparatus, it is possible to prevent abnormal vibrations, such as transverse wobbling, in a direction different from the natural vibration direction of the oscillator connected to one end of the resonator from being generated in the resonator.

In order to suppress deformation of the syringe barrel due to heat generated during cutting, it is preferable to select a material having good thermal conductivity for an ultrasonic cutting blade and a jig. Specifically, aluminum and copper are preferable materials. In a cutting method using the ultrasonic cutting apparatus, it is preferable to perform more than one cutting in the ultrasonic cutting to improve the smoothness of the surface in the same way as cutting by a lathe, etc., in which rough cutting, semi-finish cutting and finish cutting are performed in order to obtain a predetermined shape and smoothness of the surface. Although the smoothness of the surface is improved as the number of times of the cutting increases, the number of times of the cutting is preferably from 1 to 5 and more preferably from 2 to 4, in terms of productivity.

Initial Cutting (Rough Cutting) Step (1)

In the cutting method using the ultrasonic cutting apparatus, at least one rough cutting is performed to remove an unnecessary remaining gate in ultrasonic cutting in the same way as the cutting by a lathe, etc., in which rough cutting, semi-finish cutting and finish cutting are performed in order to obtain a predetermined shape and smoothness of the surface. In this process, if the initial cutting is the final cutting (if only one cutting is performed), a volume to be removed is large and a large load is required for cutting and therefore burrs are likely to occur.

Final Cutting (Finish Cutting) Step (2)

Figure 4:
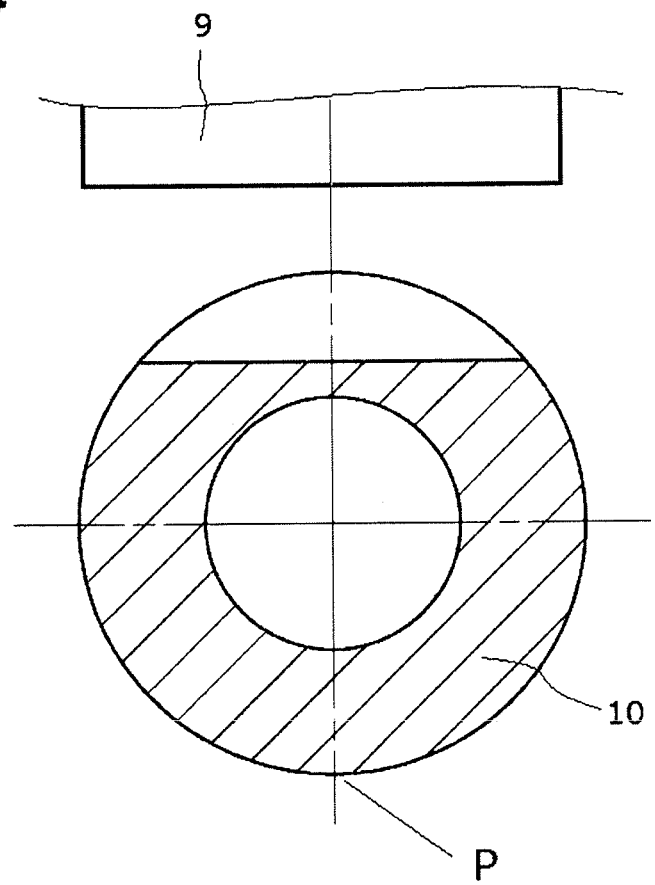
FIG. 4 is a cross-sectional view showing a nozzle part cutting position after cutting part of a circumference of the nozzle part of the syringe barrel using an ultrasonic cutting apparatus and then temporarily stopping the cutting in a final cutting step (2-1) according to an embodiment of the present invention.
Figure 5:
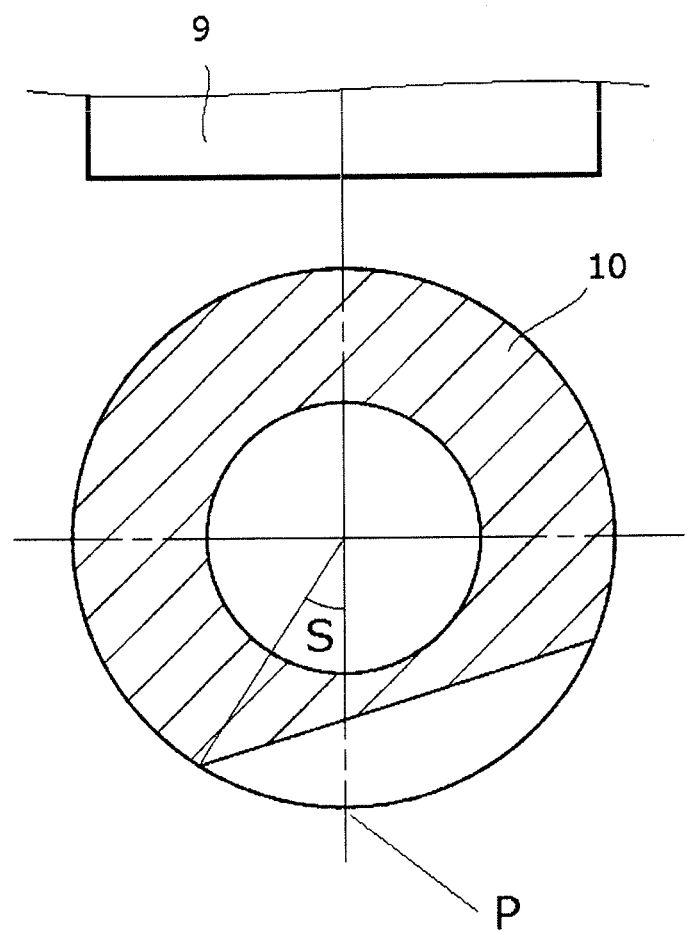
FIG. 5 is a cross-sectional view showing the nozzle part cutting position before cutting an uncut portion in a final cutting step (2-2) according to an embodiment of the present invention.

As the final step of the cutting, final cutting (finish cutting) is performed. In the final cutting step (2), first, in step (2-1), the ultrasonic cutting apparatus is used to cut part of a circumference of the nozzle part of the syringe barrel and then the cutting is temporarily stopped as shown in FIG. 4 and then in step (2-2), an uncut portion 10 is cut in a state in which an arc of the outer diameter of the uncut portion does not exist at an intersection P, which is more distant from an ultrasonic cutting blade surface, from among two intersections between an outer diameter circle of the cross-section of the nozzle part and a line segment that is perpendicular to the ultrasonic cutting blade surface (i.e., to a line defining the cutting edge, that is to say, perpendicular to the cutting edge) and passes the center of the outer diameter circle of the cross-section of the nozzle part. If the above step is omitted and the cutting is performed without stopping temporarily after starting cutting from one end of the circumference of the nozzle part, the uncut portion 10 in the remaining gate at the nozzle part, which has been softened due to heat, will yield to the self-weight and become deformed at a cutting end edge and, in addition, the molten resin is forced outward and causes the generation of burrs. Thus, by rotating the syringe barrel after cutting part of the circumference of the nozzle part so that the already-cut end is positioned on the opposite side of the ultrasonic cutting blade 9 and then performing cutting, it is possible to prevent the deformation due to the self-weight and to prevent a molten resin, which otherwise causes burrs at the cutting end edge, from being extended over the already-cut surface by the blade surface, and it is thereby possible to prevent the generation of burrs.

Although the position of stopping cutting in the final cutting step (2-1) can be set arbitrarily, it is possible to more appropriately suppress the deformation and burrs generated during the cutting after the rotation by stopping cutting when the ultrasonic cutting blade reaches at approximately 5% or more of the outer diameter. Furthermore, by stopping the cutting at approximately 95% or less of the outer diameter, it is possible to suppress the deformation of the uncut portion 10 and to further suppress breakage in the uncut portion 10 in the remaining gate at the nozzle part during the rotation. In addition, it is preferable to set the position of stopping cutting in a portion without a cavity on the inner side thereof, since the smoothness of the surface after cutting can be further improved. Specifically, the cutting is preferably stopped at 5 to 30% or 70 to 95% of the outer diameter and more preferably at 10 to 20% or 80 to 90% of the outer diameter.

In the final cutting step (2-2), cutting of the uncut portion 10 is started in the positional relationship in which the arc of the outer diameter of the uncut portion does not exist at the intersection P that is more distant from the ultrasonic cutting blade surface from among the intersections between the outer diameter circle of the cross-section of the nozzle part and the line segment that is perpendicular to the ultrasonic cutting blade surface and that passes the center of the outer diameter circle of the cross-section of the nozzle part. If the arc of the outer diameter of the uncut portion exists at the above-mentioned intersection (P), the ultrasonic cutting blade 9 drags the molten resin and causes the generation of burrs. An angle (S) formed by: a line segment connecting an intersection, which is more distant from the ultrasonic cutting blade surface from among intersections between the arc of the outer diameter of the uncut portion and its chord, and the center of the outer diameter circle; and the line segment that is perpendicular to the ultrasonic cutting blade and that passes the center of the outer diameter circle of the cross-section of the nozzle part is preferably from 5 to 155 degrees, more preferably from 10 to 135 degrees, and particularly preferably from 30 to 90 degrees. Although the positional relationship between the ultrasonic cutting blade 9 and the syringe barrel has to be changed for performing the final cutting step (2-2), the method thereof is not particularly limited. Specifically, the syringe barrel may be moved or rotated, or the ultrasonic cutting blade 9 may be moved, or both may be performed.

In the final cutting step (2), the cutting is preferably performed without applying a large load. In order to suppress a crack or a molten trace generated in the nozzle part after the cutting, the load is preferably from 1 to 400 N, more preferably from 10 to 300 N, and particularly preferably from 20 to 100N.

The cutting position from the previously cut surface in the final cutting step (2) is preferably from 0.01 to 1 mm, more preferably from 0.03 to 0.6 mm, and particularly preferably from 0.03 to 0.4 mm, from the viewpoint of reducing the load required for cutting and suppressing the generation of burrs.

Thermoplastic Resin Composition (b)

Appropriate known substances may be employed as a resin used for the syringe barrel 100 and a thermoplastic resin used as a thermoplastic resin composition (b) in the skin layers (the first resin layer 6 and the third resin layer 8) for the multilayer syringe barrel 200. Examples of such substances may comprise: polyolefins such as low density polyethylene, intermediate density polyethylene, high density polyethylene, linear low density polyethylene, linear very low density polyethylene, polypropylene, poly-1-butene, poly-4-methyl-1-pentene,or random or block copolymers of a-olefins such as ethylene, propylene, 1-butene and 4-methyl-1-pentene; acid-modified polyolefins such as maleic anhydride grafted polyethylene and maleic anhydride grafted polypropylene; ethylene-vinyl compound copolymers such as ethylene-vinyl acetate copolymer, ethylene-vinylalcohol copolymer, ethylene vinyl chloride copolymer, ethylene-(meta) acrylic acid copolymer and the ion cross-linked products thereof (ionomer), and ethylene-methyl methacrylate copolymer; styrene-based resins such as polystyrene, acrylonitrile-styrene copolymer and α-methylstyrene styrene copolymer; polyvinyl compounds such as polymethyl acrylate and polymethyl methacrylate; polyamides such as nylon 6, nylon 66, nylon 610, nylon 12, nylon 6IT and polymetaxylyleneadipamide (MXD6); polyesters such as polyethylene terephthalate (PET), polybutylene terephthalate (PBT), polytrimethylen terephthalate (PTT), polyethylene naphthalate (PEN), glycol-modified polyethylene terephthalate (PETG), polyethylene succinate (PES), polybutylene succinate (PBS), polylactic acid, polyglycolic acid, polycaprolactone and polyhydroxyalkanoate; polycarbonates; polyethers such as polyethylene oxide; cycloolefin copolymers (COC) being copolymers formed from norbornene and olefin such as ethylene as raw materials and copolymers formed from tetracyclododecene and olefin such as ethylene as raw materials; cycloolefin polymers (COP) being polymers obtained by subjecting norbornene to ring-opening polymerization and to hydrogenation; and mixtures thereof. It should be noted that the thermoplastic resin composition(s) (b) may be used alone or in combination.

It is preferable for the thermoplastic resin composition (b) to have properties excellent in chemical resistance, elution resistance and impact resistance for the purpose of storing drug solutions. In addition, it is more preferable for the thermoplastic resin composition (b) to have water vapor barrier property and the thermoplastic resin composition (b) is preferably selected from barrier resins that can satisfy water vapor permeability of 1.0 g·mm/m²·day or less, such value being obtained by a method compliant with JIS K 7126. Particularly preferable substances are cycloolefin copolymers (COC) being copolymers formed from norbornene and olefin such as ethylene as raw materials and copolymers formed from tetracyclododecene and olefin such as ethylene as raw materials, and cycloolefin polymers (COP) being polymers obtained by subjecting norbornene to ring-opening polymerization and to hydrogenation are also preferable. Such COC and COP are described in, for example, JPH05-300939 A and JPH05-317411 A.

The syringe barrel and an object to be stored therein may be subjected to sterilization treatment before or after filling, depending on the properties of the object to be stored, by a method suitable for the object to be stored. Examples of the sterilization methods may comprise: heat sterilization such as hot water treatment at 100° C. or lower, compressed hot water treatment at 100° C. or higher and high-temperature heating treatment at 121° C. or higher; electromagnetic sterilization using ultraviolet rays, microwave, gamma rays, etc.; gas treatment using ethylene oxide, etc.; and chemical sterilization using hydrogen peroxide, hypochlorous acid, etc. In accordance with the sterilization method, a resin(s) which is resistant to the sterilization method is preferably selected for a barrier thermoplastic resin composition (a) and the thermoplastic resin composition (b).

Barrier Thermoplastic Resin Composition (a)

A resin which is used as the barrier thermoplastic resin composition (a) in the core layer (second resin layer 7) of the multilayer syringe barrel 200 is at least one type selected from the group consisting of polyolefin, polyester, polyamide, ethylene-vinylalcohol copolymer, plant-derived resins and chlorine-based resins and, in terms of the oxygen barrier property, it is preferably selected from barrier resins that can satisfy oxygen permeability of 0.5 cc·mm/m²·day·atm or less, such value being obtained by a method compliant with JIS K 7126. In addition, the barrier thermoplastic resin composition (a) is preferably an amorphous resin from the viewpoint of transparency, so that the content thereof is easily visible. Furthermore, the barrier thermoplastic resin composition (a) is preferably an oxygen-absorbing resin composition. No matter how appropriately gas replacement is performed when the syringe barrel is filled with a drug solution, oxygen contained in air bubbles introduced during the filling and oxygen dissolved in a solution of the content cannot be completely removed. If the barrier thermoplastic resin composition (a) is an oxygen-absorbing resin composition, it is capable of not only absorbing the dissolved oxygen but also completely eliminating even a minute amount of oxygen that has penetrated through a wall of the container and entered the container. Examples of preferable oxygen-absorbing resin compositions comprise an oxygen-absorbing resin composition containing a polyester compound and a transition metal catalyst described in WO2013/077436.

Manufacturing Method etc.

The above-described monolayer syringe barrel 100 and multilayer syringe barrel 200 may be manufactured, without particular limitation, by apparatuses capable of performing known injection molding or co-injection molding, depending on the properties of various materials, the targeted shape, etc.

The monolayer syringe barrel 100 can be manufactured by subjecting the thermoplastic resin composition (b) to injection molding so as to be molded into the above-mentioned shape. The multilayer syringe barrel 200 can be manufactured by performing the co-injection molding with the thermoplastic resin composition (b) as a skin side and the barrier thermoplastic resin composition (a) as a core side so as to form the syringe barrel 200.

When a multilayer syringe barrel is manufactured, specifically, an injection molding machine having two injection cylinders (having a cylinder temperature of 200 to 320° C.) is used to first inject a certain amount of the thermoplastic resin composition (b) from an injection cylinder on a skin side and to then inject a certain amount of the barrier thermoplastic resin composition (a) from an injection cylinder on a core side, via a hot-runner mold, into a gate provided at a nozzle tip of the syringe barrel in a cavity. The thermoplastic resin composition (b) which is injected first is cooled by the cavity and a wall surface of the core mold and forms a skin layer, and the barrier thermoplastic resin composition (a) forms a core layer which is provided between the skin layers. Then, the multilayer syringe barrel 200 can be manufactured by stopping the injection of the barrier thermoplastic resin composition (a) and then again injecting a certain amount of thermoplastic resin composition (b).

EXAMPLE 1

Although Examples and Comparative Examples will now be described in order to further explain the present invention, the present invention is not limited thereto. In the Examples and Comparative Examples, various types of physical values were measured by way of the measurement methods and measurement apparatuses which will be described below.

In the following descriptions, while describing the Examples and the Comparative Examples, six cutting methods indicated as <A> to <F> in Table 1 will be described as the cutting methods of the remaining gate at the nozzle part using the ultrasonic cutting apparatus. It should be noted that the "rotation" as used herein refers to the process of temporarily stopping the cutting of a syringe barrel, rotating the syringe barrel, and then restarting the cutting. "Rotation" also comprises rotating the ultrasonic cutting blade 9 relative to the syringe barrel, as a matter of course.

TABLE 1

| Cutting Pattern | Initial Cutting (Rough Cutting) | | Final Cutting (Finish Cutting) | |
| --- | --- | --- | --- | --- |
| | Performed/Not performed | Rotation | Performed/Not performed | Rotation |
| <A> | Not performed | — | Performed | Not performed |
| <B> | Not performed | — | Performed | Performed |
| <C> | Performed | Not performed | Performed | Not performed |
| <D> | Performed | Not performed | Performed | Performed |
| <E> | Performed | Performed | Performed | Not performed |
| <F> | Performed | Performed | Performed | Performed |

(Inspection of Cut Surface)

The inspection of cut surfaces was performed using a digital microscope (product name "VHX1000" manufactured by KEYENCE CORPORATION) to evaluate the smoothness of the surfaces, the generation of burrs and melting, and the generation of cracks. The smoothness of surfaces was evaluated through visual observation of the appearance and measurement of the surface roughness (arithmetic average roughness) Ra measured using a surface roughness measuring instrument "SURFCOM 3000" manufactured by TOKYO SEIMITSU CO., LTD.

EXAMPLE 1

Cutting Pattern <E>

Injection Molding of Multilayer Syringe Barrel

A multilayer syringe barrel having the same shape as the multilayer syringe barrel 200 of FIG. 2 was prepared using an injection molding machine (product type: ASB-12N/10 manufactured by NISSEI ASB MACHINE CO., LTD.). The specific shape was a shape having an interior capacity of 5 cc which is compliant with ISO 11040-6. The molding conditions were adjusted so that the ratio of a resin injection amount for the core layer to a resin injection amount for the skin layer was 30 mass %, a start edge of the core layer was located within an area between a rear end of a gasket insertion position and the flange 5, and an end edge of the core layer was located at a position apart from the position of a gate cut. Specifically, the thermoplastic resin composition (b) constituting the skin layer was first injected from an injection cylinder, then a certain amount of the barrier thermoplastic resin composition (a) constituting the core layer was injected from another injection cylinder, the injection of the barrier thermoplastic resin composition (a) was stopped, and a certain amount of the thermoplastic resin composition (b) was injected so as to fill a cavity in an injection mold to thereby manufacture a multilayer syringe barrel having three layers of the thermoplastic resin composition (b)/the barrier thermoplastic resin composition (a)/ the thermoplastic resin composition (b). As the barrier thermoplastic resin composition (a), an oxygen-absorbing composition obtained by dry-blending 0.02 parts by mass of cobalt (II) stearate on the basis of 100 parts by mass of aromatic polyamide resin (product name "MX nylon S6007" manufactured by MITSUBISHI GAS CHEMICAL COMPANY, INC.). As the thermoplastic resin composition (b), cycloolefin polymer resin (product name "ZEONEX 690R" manufactured by ZEON CORPORATION, hereinafter referred to as "COP") was used.

Cutting of Remaining Gate at Nozzle Part

An ultrasonic cutter "UC1000LS" manufactured by ADWELDS CORPORATION having a mechanism for suppressing abnormal vibrations was used to cut a remaining gate at a nozzle part after molding. The remaining gate was cut such that the diameter of the nozzle part after cutting fell within the values specified in ISO 594-1 (i.e. φ3.976+/−0.051). The surface roughness (arithmetic average roughness) Ra of a cut surface of the multilayer syringe barrel after cutting was measured and evaluated as passed if the surface roughness was equal to or lower than Ra 3.0 μm as specified in JIS B 0031, which is generally required in cuttings using rotary blades and grinding wheels. The cut surface was further inspected to check the smoothness of the surface and the generation of melting. The results are shown in Tables 2 and 3 and the evaluation items, evaluation criteria, etc., are shown in Table 4.

It should be noted that the "cutting time" was employed as a new evaluation item. Since the (relative) rotation of a syringe barrel requires some additional time, the evaluation was also performed in terms of time. In addition, since the way of cutting during the final cutting affects a finished surface, the cutting load in the final cutting was evaluated as a cutting load.

EXAMPLES 2-12

Cutting Patterns <B>, <C>, <D> and <F>

A multilayer syringe barrel was subjected to cutting after molding in the same way as in Example 1, except that the cutting conditions (cutting steps) were changed to those indicated in Tables 2 and 3, and the evaluation was conducted. The results are shown in Tables 2 and 3.

EXAMPLES 13-17

Cutting Patterns <A>, <C>, <E> and <F>

A multilayer syringe barrel was subjected to cutting after molding in the same way as in Example 1, except that polypropylene resin (PPM R021 manufactured by Total, hereinafter referred to as "PP") was used as the thermoplastic resin composition (b) instead of COP, and the cutting conditions (cutting steps) were changed to those indicated in Tables 2 and 3, and the evaluation was conducted. The results are shown in Tables 2 and 3.

EXAMPLES 18 and 19

Cutting Patterns <C> and <F>

Manufacturing of Monolayer Syringe Barrel

A monolayer syringe barrel having the same shape as the monolayer syringe barrel 100 of FIG. 1 was prepared using an injection molding machine (product type: ASB-12N/10, manufactured by NISSEI ASB MACHINE CO., LTD.). The specific shape was a shape having an interior capacity of 5 cc which is compliant with ISO 11040-6. The monolayer syringe barrel was manufactured by injecting the cycloolefin polymer resin used in Example 1 from an injection cylinder to fill a cavity in an injection mold. The monolayer syringe barrel was subjected to cutting in the same way as in Example 1, except that the cutting conditions (cutting steps) were changed to those indicated in Tables 2 and 3, and the evaluation was conducted.

COMPARATIVE EXAMPLES 1-3

A multilayer syringe barrel was subjected to cutting after molding in the same way as in Example 1, except that the apparatus used for cutting the remaining gate at the nozzle part after the molding was changed to an ultrasonic cutter having no mechanism for suppressing abnormal vibrations, "USW334" manufactured by HONDA ELECTRONICS CO., LTD., and the cutting conditions (cutting steps) were changed to those indicated in Tables 2 and 3, and the evaluation was conducted. The results are shown in Tables 2-1 to 2-4 (see FIGS. 6A to 6D), Table 3 (see FIG. 7), and Table 4 (see FIG. 8).

REFERENCE SIGNS LIST

100: monolayer syringe barrel
200: multilayer syringe barrel
1: nozzle part
2: shoulder part
3: cylindrical part
4: cylindrical part base end
5: flange
6: first resin layer (skin layer)
7: second resin layer (core layer)
8: third resin layer (skin layer)
9: ultrasonic cutting blade
10: uncut portion

What is claimed is:
1. A manufacturing method of a syringe barrel that is injection-molded from a nozzle tip, the method comprising:

cutting a remaining gate at a nozzle part of the syringe barrel using an ultrasonic cutting apparatus having a abnormal vibration suppressing cutter, wherein during the cutting of the remaining gate at the nozzle part of the syringe barrel:

performing the cutting of the remaining gate a plurality of times;

temporarily stopping the cutting of the remaining gate after cutting part of a circumferential surface of the nozzle part of the syringe barrel;

relatively rotating an ultrasonic cutting blade of the ultrasonic cutting apparatus and the syringe barrel while the cutting of the remaining gate is temporarily stopped; and cutting with the ultrasonic cutting blade another portion of the remaining gate along the circumferential surface of the nozzle part.

2. The manufacturing method according to claim 1, comprising:

in a final cutting step, temporarily stopping cutting after the cutting of the part of the circumferential surface of the nozzle part of the syringe barrel using the ultrasonic cutting apparatus; and relatively rotating the ultrasonic cutting blade and the syringe barrel to a positional relationship in which an arc of an outer diameter of an uncut portion of the remaining gate does not exist at an intersection that is more distant from an ultrasonic cutting blade surface of the ultrasonic cutting blade from among two intersections between an outer diameter circle of a cross-section of the nozzle part and a line segment that is perpendicular to a cutting edge of the ultrasonic cutting blade and that passes a center of the outer diameter circle of the cross-section of the nozzle part, and then performing cutting of the uncut portion of the remaining gate.

3. The manufacturing method according to claim 1, comprising, when a final cutting step is performed after the remaining gate at the nozzle part is cut with a finishing allowance being left in an initial cutting step, during the cutting of the remaining gate at the nozzle part in the initial cutting step, temporarily stopping the cutting after cutting part of the remaining gate at the nozzle part, relatively rotating the ultrasonic cutting blade and the syringe barrel, and cutting another portion of the remaining gate at the nozzle part.

4. The manufacturing method according to claim 1, wherein the syringe barrel has a multilayer structure having at least three resin layers.

5. The manufacturing method according to claim 1, wherein, during a final cutting of the syringe barrel, a load applied to an ultrasonic cutting blade of the ultrasonic cutting apparatus is from 1 to 400 N.

6. The manufacturing method according to claim 1, wherein, in a final cutting step, a distance from a previously cut surface of the remaining gate to a cutting position in the final cutting step is from 0.1 to 1 mm.

* * * * *